(12) United States Patent
Predal

(10) Patent No.: US 7,740,885 B2
(45) Date of Patent: Jun. 22, 2010

(54) NUTRACEUTICAL AND PHARMACEUTICAL COMPOSITIONS AND THEIR USES

(75) Inventor: Ludovic Predal, Saint Etienne Cedex (FR)

(73) Assignee: Fresaxal Holding, Inc., Montreal, Quebec (CA)

( * ) Notice: Subject to any disclaimer, the term of this patent is extended or adjusted under 35 U.S.C. 154(b) by 307 days.

(21) Appl. No.: 10/554,155

(22) PCT Filed: May 22, 2003

(86) PCT No.: PCT/FR03/01544

§ 371 (c)(1),
(2), (4) Date: Oct. 20, 2005

(87) PCT Pub. No.: WO03/097033

PCT Pub. Date: Nov. 27, 2003

(65) Prior Publication Data

US 2007/0128292 A1    Jun. 7, 2007

(30) Foreign Application Priority Data

May 22, 2002  (FR) .................................. 02 06205

(51) Int. Cl.
*A01N 43/04* (2006.01)
(52) U.S. Cl. ......................................... 424/725; 514/23
(58) Field of Classification Search ................. 424/725; 514/23
See application file for complete search history.

(56) References Cited

U.S. PATENT DOCUMENTS

| | | | | |
|---|---|---|---|---|
| 5,223,282 A | * | 6/1993 | Patel et al. ...................... | 426/3 |
| 5,312,834 A | * | 5/1994 | Yeo ............................... | 514/560 |
| 5,756,088 A | * | 5/1998 | Matsuura et al. ............. | 424/93.4 |
| 6,077,828 A | * | 6/2000 | Abbruzzese et al. .......... | 514/21 |
| 2002/0034562 A1 | * | 3/2002 | Sundram et al. ............... | 426/2 |
| 2006/0111254 A1 | * | 5/2006 | Makadia et al. ............. | 508/459 |

FOREIGN PATENT DOCUMENTS

| | | |
|---|---|---|
| EP | 0266323 | 5/1988 |
| EP | 0585027 | 3/1994 |
| EP | 0611568 | 8/1994 |
| EP | 0784694 | 7/1997 |
| EP | 1155620 | 11/2001 |
| EP | 1181870 | 2/2002 |
| FR | 2637910 | 4/1990 |
| FR | 2721517 | * 12/1995 |
| JP | 03297364 | * 12/1991 |
| JP | 06-169735 | 6/1994 |
| JP | 06-237734 | 8/1994 |
| WO | 9319624 | 10/1993 |
| WO | 0178530 | 10/2001 |

OTHER PUBLICATIONS

Haagsma et. al., "Preparation of an ω3 fatty acid concentrate from cod liver oil." Journal of American Oil Chemists' Soc., 1982, pp. 117-118, vol. 59. Urbana, IL.

Taguchi, K, et. al., "Preservability and utilization of powdered Na-linolenic acid with egg white." Bioscience, Biotechnology, and Biochemistry, 1992, Dept. of Home Sci., Koka Women's Jr. Coll., vol. 56, No. 4, pp. 672-673. Kyoto, Japan.

International Search Report for international application No. PCT/FR03/001544 issued by the International Searching Authority mailed on Nov. 20, 2003.

* cited by examiner

*Primary Examiner*—Ruth A Davis
(74) *Attorney, Agent, or Firm*—Michael A. Davitz

(57) ABSTRACT

The invention relates to organic chemistry area and more particularly to the polyunsaturated fatty acids area. The invention specifically relates to nutraceutical or pharmaceutical compositions rich in unsaturated fatty acids, characterized in that they contain free or combined alpha-linolenic acid, associated with fatty acids having five and six double-bonds, admixed with a diluent or vehicle suitable for oral administration. These compositions are used for preventing or treating human or animal cardio-vascular diseases, at a dose ranging from 800 to 1.000 mg of a-linolenic acid, from 80 to 120 mg of eicosapentaenoic acid and from 800 to 1.000 mg of docosahexaenoic acid.

13 Claims, No Drawings

NUTRACEUTICAL AND PHARMACEUTICAL COMPOSITIONS AND THEIR USES

This application is a 371 of PCT/FR03/01544 filed May 22, 2003.

The present invention relates to organic chemistry area and more particularly to the polyunsaturated fatty acids area.

The present invention relates to nutraceutical or pharmaceutical compositions rich in unsaturated fatty acids, intended for preventing or treating human or animal cardiovascular diseases.

The invention specifically relates to nutraceutical or pharmaceutical compositions rich in unsaturated fatty acids, characterized in that they contain free or combined α-linolenic acid, in admixture with fatty acids having five or six double-bonds.

The invention effectively relates to a natural product rich in α-linolenic acid, such as a vegetal oil and more precisely kiwi seed oil, linseed oil, cameline oil, etc . . . .

α-linolenic acid can also be employed as a chemical product. It may be pure or salified, for example as the sodium or calcium salt. It may also be esterified, such as methyl, ethyl or glyceryl α-linoleate, or adsorbed in a cellulose derivative such as hydroxyethylcellulose, hydroxypropyl methyl cellulose or in cyclodextrins.

Fatty acids with five double-bonds are typically eicosapentaenoic acid, abundantly found in fish oils such as halibut, cod liver, haddock, tuna, sardine or shark oil.

The fatty acids with six double-bonds also come from fish oils, notably rich in docosahexaenoic acid. A well-known source of such a fatty acid is tuna or sardine oil.

Polyunsaturated fatty acids may also exist as concentrates, obtained for example by oil molecular distillation, which provide preparations containing up to 50% of a specific fatty acid.

Polyunsaturated fatty acids may also be obtained by supercritical fluid extraction from oils, using pressure variations. Polyunsaturated fatty acids may be selectively extracted by this means (See French patent 2.637.910 or N. Hagsma et. al., J. Am. Oil Chem. Soc. 1982, 59, 147).

Ribes oils, such as currant or blackcurrant seed oil, may also be concentrated in α-linolenic acid, by forming a complex with urea.

Fish oils may also be enriched in eicosapentaenoic or docosahexaenoic acid by forming a complex with urea (see European patent application A1-96904125.0).

It is possible to mix different fish oils in the compositions according to the invention, in order to increase the eicosapentaenoic or docosahexaenoic acid rate. Shark or sardine oil are precious sources of these very unsaturated fatty acids.

The compositions according to the invention are defined by a specific ratio between the different fatty acids of the mixture. α-linolenic acid is the main compound, from 70 to 90% of the global fatty acid weight. Eicosapentaenoic acid constitutes 10 to 20% and docosahexaenoic acid 25 to 35% of this global weight.

Typically, a composition according to the invention contains from 800 to 1.000 mg of α-linolenic acid, from 80 to 120 mg of eicosapentaenoic acid and from 250 to 300 mg of docosahexaenoic acid. The γ-linolenic acid rate can possibly be comprised between 100 and 120 mg by unit dose.

As an example, associations of different polyunsaturated acids have already been described, such as a granulate containing from 2 to 7% of marine or vegetal oil comprising γ-linolenic, eicosapentaenoic and/or docosahexaenoic acid, as well as other oils and a water-soluble vehicle. These granulates are used as tablets in pharmaceuticals, as alimentary supplements and products and as cattle food (see European patent 0.266.323).

Already described has also been the use of fatty acids such as γ-linolenic acid and/or its main metabolites, particularly dihomo-γ-linolenic acid, and/or eicosapentaenoic (EPA), stearidonic or docosahexaenoic acid (DHA). The polyunsaturated fatty acids are used in a pure, salified or under another pharmacologically acceptable form, to manufacture a drug intended for preventing or treating a human and animal soft tissue or vessel abnormal calcification (see European patent 0.585.027-A1).

However, none of these documents describes the association of α-linolenic acid and these two polyunsaturated fatty acids obtained from fish oil. α-linolenic acid plays a very specific role: it does not lead to prostaglandins but, through the action of specific desaturases and elongases, leads to n-3 polyunsaturated fatty acids of higher molecular weight.

The problem with a composition according to the invention was to find a starting material containing high amounts of α-linolenic acid, preferably over 50% of the oil weight. Such a source of α-linolenic acid is mainly constituted by kiwi seed, linseed or cameline oil.

Kiwi seed oil is an abundant starting material, extracted from kiwi seeds by solvent-free specific extraction or by solvent extraction. The recommended daily intake of α-linolenic acid is approximately 2 g per day. The corresponding amount of kiwi seed oil is 3 ml.

The compositions according to the invention are valuable in therapeutics and in dietetics for preventing and treating artheromatosis. The interest for polyunsaturated fatty acids come from an epidemiological study made by Danish scientists on a population sample of Groenland Eskimos, whose cardio-coronary disease rate is particularly low. This effect has been attributed to the marine polyunsaturated fatty acids (especially EPA and DHA) contained in their food.

The compositions according to the invention are administrated in the forms of capsules containing up to 1.500 mg of oily compound, given from 1 to 3 units per day.

They also may be designed as granules, powders on a powdery carrier or drinkable emulsions. The problem with the manufacture of such compositions is to preserve them from oxidation by atmospheric oxygen and from light decomposition. The use of tinted glass and coloured capsules lowers these effects. The adding of an antioxidant, a natural one such as tocopherols or a synthetic one such as BHA or TBA, prevents the oxidation or peroxidation phenomena.

A preferred composition according to the invention is that which contains, for a 1.500 mg capsule, 900 mg of α-linolenic acid, 100 mg of EPA, 270 mg of DHA and optionally 115 mg of γ-linolenic acid, the rest being a neutral oil, stable towards rancidity.

The following examples are intended to give a better description of the invention and are by no means limiting it.

EXAMPLE 1

α-Linolenic Acid Soft Capsules

Kiwi seed oil corresponding to 900 mg of α-linolenic acid;

Sardine oil corresponding to 100 mg of eicosapentaenoic acid;

Tuna oil corresponding to 270 mg of docosahexaenoic acid;

Borage oil corresponding to 115 mg of γ-linolenic acid;

Almond oil q.s. for a capsule weighing 1.500 mg.

EXAMPLE 2

α-Linolenic Acid Soft Capsules
Kiwi seed oil corresponding to 1.000 mg of α-linolenic acid;
Eicosapentaenoic and docosahexaenoic acid triglyceride concentrate, corresponding to 80 mg of eicosapentaenoic acid and to 300 mg of docosahexaenoic acid;
Peanut oil q.s. for a soft capsule weighing 1.500 mg.

EXAMPLE 3

α-Linolenic Acid Soft Capsules
Kiwi seed oil corresponding to 800 mg of α-linolenic acid;
Sardine oil concentrate corresponding to 100 mg of eicosapentaenoic acid;
Halibut oil concentrate corresponding to 300 mg of docosahexaenoic acid;
Cotton seed oil q.s. for a soft capsule weighing 1.500 mg.

EXAMPLE 4

α-Linolenic Acid Drinkable Emulsion
Kiwi seed oil corresponding to 800 mg of α-linolenic acid;
Sardine oil corresponding to 100 mg of eicosapentaenoic acid;
Shark oil corresponding to 200 mg of docosahexaenoic acid;
Corn oil, 10 ml;
Polysorbate 60, 8 ml;
Glucose syrup, 20 ml;
Water q.s. for 100 ml;
Apricot aroma q.s.

EXAMPLE 5

α-Linolenic Acid Drinkable Emulsion
Kiwi seed oil, 25 g;
Sardine oil, 12 g;
Tuna oil, 20 g;
Polyethyleneglycol stearate, 2 g;
Polyethyleneglycol, 12 g;
Tert-butylhydroxyanisole, 1 g;
Aroma q.s.;
Ethanol, 20 g;
Water q.s. for 100 g.

What is claimed is:

1. A pharmaceutical composition comprising from about 800 mg to about 1000 mg of α-linolenic acid, from about 80 mg to about 120 mg of eicosapentaenoic acid, from about 250 mg to about 300 mg of docosahexaenoic acid and an antioxidant.

2. The pharmaceutical composition of claim 1 further comprising from about 100 mg to about 120 mg of γ-linolenic acid.

3. The pharmaceutical composition of claim 1 wherein the antioxidant is selected from the group consisting of butylhydroxyanisole (BHA), thiobarbituric acid (TBA) or tocopherol.

4. The pharmaceutical composition of claim 3 wherein the antioxidant is tocopherol.

5. The pharmaceutical composition of claim 1 wherein the pharmaceutical composition is a capsule.

6. The pharmaceutical composition of claim 5 wherein the capsule weighs about 1500 mg.

7. A pharmaceutical composition comprising from about 53% (w/w) to about 66.7% (w/w) of α-linolenic acid, from about 5.3% (w/w) to about 6.7% (w/w) of eicosapentaenoic acid and from about 13.3% (w/w) to about 20% (w/w) of docosahexaenoic acid and an antioxidant.

8. The pharmaceutical composition of claim 7 further comprising about 7.7% (w/w) of γ-linolenic acid.

9. The pharmaceutical composition of claim 7 wherein the antioxidant is selected from the group consisting of butylhydroxyanisole (BHA), thiobarbituric acid (TBA)or tocopherol.

10. The pharmaceutical composition of claim 9 wherein the antioxidant is tocopherol.

11. The pharmaceutical composition of claim 7 wherein the composition is in the form of a powder or granule.

12. The pharmaceutical composition of claim 7 wherein the pharmaceutical composition is stored in tinted glass.

13. The pharmaceutical composition of claim 7 wherein the pharmaceutical composition is stored in a coloured capsule.

* * * * *